US006554985B2

(12) United States Patent
Ruiz-Martinez et al.

(10) Patent No.: US 6,554,985 B2
(45) Date of Patent: *Apr. 29, 2003

(54) METHODS AND FORMULATIONS FOR THE SEPARATION OF BIOLOGICAL MACROMOLECULES

(75) Inventors: Marie C. Ruiz-Martinez, New Haven, CT (US); Jan Berka, New Haven, CT (US); John W. Simpson, Madison, CT (US)

(73) Assignee: CuraGen Corporation, New Haven, CT (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/374,174

(22) Filed: Aug. 13, 1999

(65) Prior Publication Data

US 2002/0009721 A1 Jan. 24, 2002

Related U.S. Application Data

(60) Provisional application No. 60/107,798, filed on Nov. 10, 1998.

(51) Int. Cl.[7] .................. B01D 57/02; B01D 59/42; B01D 59/50; C02F 1/40; C12M 1/34

(52) U.S. Cl. .............. 204/451; 204/450; 204/456; 204/606; 435/287.2

(58) Field of Search .................. 435/6, 283.1, 285.2, 435/91.1, 287.1, 287.2, 288.4; 422/68.1; 204/450, 451

(56) References Cited

U.S. PATENT DOCUMENTS

| 4,999,340 A | * | 3/1991 | Hoffman et al. ............... 514/23 |
| 5,503,722 A | | 4/1996 | Guttman |
| 5,534,123 A | | 7/1996 | Bashkin et al. |
| 5,552,028 A | * | 9/1996 | Madabhushi et al. ....... 204/451 |

FOREIGN PATENT DOCUMENTS

| EP | 0 809 103 A2 | 11/1997 |
| WO | WO 93/15394 | 8/1993 |
| WO | WO 95/06668 | 3/1995 |

OTHER PUBLICATIONS

Ruiz–Martinez et al., DNA sequencing by capillary electrophoresis with replaceable linear polyacrylamide and laser–induced fluorescence detection. Anal. Chem. 65,2851–2858, 1993.*

Rosenblum et al., Improved single–strand DNA sizing accuracy in capillary electrophoresis. Nucleic Acids Res. 25, 3925–3929, 1997.*

Ruiz–Martinez et al., DNA sequencing by capillary electrophoresis with replaceable linear polyacrylamide and laser–induced fluorescence detection. Anal. Biochem. 65, 2851–2858, 1993.*

Rosenblum et al., Improved single–strand DNA sizing accuracy in capillary electrophoresis. Nucleic Acids Res. 25, 3925–3929, 1997.*

George et al., Capillary electrophoresis methodology for identification of cancer related gene expression patterns of fluorescent differential display polymerase chain reaction. J. Chromatogr. B 695, 93–102, 1997.*

Chen et al., Affinity electrophoresis in gles containing hydrophobic substituents. J. Biol. Chem. 256, 9221–9223, 1981.*

Sambrook et al., Molecular Cloning, A Laboratory Manual, Second Edition, p. 6.7, 1989, Published by Cold Spring Harbor Laboratory Press.*

Ruiz–Martinez et al., DNA sequencing by capillary electrophoresis with replaceable linear polyacrylamide and laser–induced fluorescence detection. Anal. Chem. 65,2851–2858, 1993.*

Rosenblum et al., Improved single–strand DNA sizing accuracy in capillary electrophoresis. Nucleic Acids Res. 25, 3925–3929, 1997.*

Atha, (1998). "Characterization of DNA standards by capillary electrophoresis." *Electrophoresis* 19(8–9): 1428–35.

Berka, et al. (1995). "Sequence dependent migration behavior of double–stranded DNA in capillary electrophoresis." *Electrophoresis* 16(3): 377–88.

Dimo–Simonin, N.,F. Grange, et al. (1998). "Forensic validation of the short tandem repeat HUMACTBP2 using capillary electrophoresis." *Electrophoresis* 19(2): 256–61.

Fleischmann, et al. (1995). "Whole–genome random sequencing and assembly of Haemophilus influenza Rd [see comments]." *Science* 269(5223): 496–512.

Goetzinger, et al. (1998). "Characterization of high molecular mass linear polyacrylamide powder prepared by emulsion polymerization as a replaceable polymer matrix for DNA sequencing by capillary electrophoresis." *Electrophoresis* 19(2): 242–8.

Isenberg, et al. (1998). "Analysis of two multiplexed short tandem repeat systems using capillary electrophoresis with multiwavelength fluorescence detection." *Electrophoresis* 19(1): 94–100.

Kleparnik, et al. (1996). "The use of elevated column temperature to extend DNA sequencing read lengths in capillary electrophoresis with replaceable polymer matrices." *Electrophoresis* 17(12): 1860–6.

(List continued on next page.)

*Primary Examiner*—Ethan Whisenant
*Assistant Examiner*—Frank Lu
(74) *Attorney, Agent, or Firm*—Mintz Levin; Ivor R. ELrifi; Cynthia A. Kozakiewicz

(57) ABSTRACT

This invention relates to methods and formulations for the separation of biological macromolecules according to their size using capillary electrophoresis with improved polyacrylamide matrixes under denaturing conditions.

32 Claims, 9 Drawing Sheets

OTHER PUBLICATIONS

Lazaruk, et al. (1998). "Genotyping of forensic short tandem repeat (STR) systems based on sizing precision in a capillary electrophoresis instrument." *Electrophoresis* 19(1): 86–93.

Levine, et al., (1963). "The Relationship of Structure to the Effectiveness of Denaturing Agents for Deoxyribonucleic Acids." *Biochemistry* 2(1): 168–175.

Mansfield, et al., (1998). "Analysis of multiplexed short tandem repeat (STR) systems using capillary array electrophoresis." *Electrophoresis* 19(1): 101–7.

Pariat, et al. (1993). "Separation of DNA fragments by capillary electrophoresis using replaceable linear polyacrylamide matrices." *J Chromatogr A* 652(1): 57–66.

Quesada, (1997). "Replaceable polymers in DNA sequencing by capillary electrophoresis." *Curr Opin Biotechnol* 8(1): 82–93.

Rosenblum, et al. (1997). "Improved single–strand DNA sizing accuracy in capillary electrophoresis." *Nucleic Acids Res* 25(19): 3925–3929.

Ruiz–Martinez, et al. (1993). "DNA sequencing by capillary electrophoresis with replaceable linear polyacrylamide and laser–induced fluorescence detection." *Anal Chem* 65(20): 2851–8.

Sealy, et al. Gel Electrophoresis of DNA. *Gel Electrophoresis of Nucleic Acids: A Practical Approach.* D. Rickwood and B. D. Hames: 51–57.

Slater, et al. (1998). "Recent developments in DNA electrophoretic separations [In Process Citation]." *Electrophoresis* 19(10): 1525–41.

Sudor, et al. (1991). "Pressure refilled polyacrylamide columns for the separation of oligonucleotides by capillary electrophoresis." *Electrophoresis* 12(12): 1056–8.

Vainer, et al. (1997). "Short tandem repeat typing capillary array electrophoresis: comparison of sizing accuracy and precision using different buffer systems." *Genomics* 41(1): 1–9.

Wenz, (1994). "Capillary electrophoresis as a technique to analyze sequence–induced anomalously migrating DNA fragments." *Nucleic Acids Res* 22(19): 4002–8.

Wenz, et al., (1998). "High–precision genotyping by denaturing capillary electrophoresis." *Genome Res* 8(1): 69–80.

PCT Notification of Transmittal of the International Search Report or the Declaration for PCT Publication WO/US99/26465.

PCT Written Opinion for PCT Publication WO/US99/26465.

* cited by examiner

QEA_157_21HEC HI i0m0 as sized by HI m1c0

| Lane Theoretical | 1 | 2 | 3 | 4 | 5 | 6 | 7 | 8 | 9 | 10 | 11 | 12 |
|---|---|---|---|---|---|---|---|---|---|---|---|---|
| 91 | 90.5 | 90.5 | 90.5 | 90.5 | 90.5 | 90.6 | 90.6 | 90.5 | 90.5 | 90.6 | 90.6 | 90.6 |
| 106 | 105.8 | 105.8 | 105.8 | 105.7 | 105.7 | 105.9 | 105.7 | 105.7 | 105.8 | 105.8 | 105.8 | 105.9 |
| 110 | 109.6 | 109.6 | 109.6 | 109.5 | 109.6 | 109.7 | 109.6 | 109.6 | 109.6 | 109.6 | 109.6 | 109.6 |
| 118 | 117.3 | 117.3 | 117.3 | 117.2 | 117.3 | 117.4 | 117.3 | 117.3 | 117.3 | 117.3 | 117.4 | 117.3 |
| 130 | 129.9 | 129.9 | 129.9 | 129.9 | 129.9 | 130.1 | 130 | 130 | 129.9 | 130 | 130 | 129.9 |
| 199 | 198.3 | 198.3 | 198.3 | 198.3 | 198.3 | 198.3 | 198.3 | 198.3 | 198.3 | 198.3 | 198.3 | 198.3 |
| 211 | 210.8 | 210.7 | 210.6 | 210.7 | 210.7 | 210.7 | 210.7 | 210.7 | 210.8 | 210.7 | 210.7 | 210.7 |
| 217 | 216.7 | 216.8 | 216.8 | 216.8 | 216.9 | 216.9 | 216.8 | 216.8 | 216.8 | 216.8 | 216.8 | 216.9 |
| 252 | 251.4 | 251.3 | 251.2 | 251.3 | 251.3 | 251.4 | 251.3 | 251.3 | 251.4 | 251.3 | 251.2 | 251.4 |
| 256 | 256 | 256 | 255.9 | 255.9 | 256 | 256 | 255.9 | 255.9 | 256 | 255.9 | 255.8 | 256 |
| 268 | 267.7 | 267.6 | 267.5 | 267.6 | 267.7 | 267.7 | 267.6 | 267.6 | 267.7 | 267.6 | 267.6 | 267.6 |
| 271 | 270.4 | 270.3 | 270.2 | 270.3 | 270.3 | 270.3 | 270.3 | 270.4 | 270.4 | 270.4 | 270.2 | 270.3 |
| 331 | 331.3 | 331.3 | 331.3 | 331.3 | 331.3 | 331.3 | 331.2 | 331.3 | 331.4 | 331.2 | 331.2 | 331.3 |
| 429 | 429.1 | 429.1 | 429.1 | 429 | 429.1 | 429.1 | 429.1 | 429.1 | 429.1 | 429.2 | 429.2 | 429.2 |
| 452 | 453 | 453 | 452.8 | 452.8 | 452.9 | 453 | 452.9 | 452.9 | 452.9 | 452.9 | 452.9 | 452.9 |
| 520 | 518.1 | 518.1 | 518.2 | 518.1 | 517.6 | 517.8 | 517.8 | 518.1 | 518.1 | 518 | 518.1 | 518.2 |

Fig. 9

SEQUENCE LISTING

```
<160> NUMBER OF SEQ ID NOS: 5

<210> SEQ ID NO 1
<211> LENGTH: 1069
<212> TYPE: DNA
<213> ORGANISM: Bacteriophage M13mp18
<220> FEATURE:
<223> OTHER INFORMATION: Wherein an "N" between residues 811 to 1069
      may be G, A, T or C

<400> SEQUENCE: 1
gccagtgcaa gcttgcatgc tgcaggtcga tctagaggat cccgggtacg agctcgaatt      60
cgtaatcatg gtcatagctg tttcctgtgt gaaattgtta tccgctcaca attccacaca     120
acatacgagc cggaagcata aagtgtaaag cctggggtgc ctaatgagtg agctaactca     180
cattaattgc gttgcgctca ctgcccgctt tccagtcggg aaacctgtcg tgccagctgc     240
attaatgaat cggccaacgc gcggggagag gcggtttgcg tattgggcgc cagggtggtt     300
tttcttttca ccagtgagac gggcaacagc tgattgccct tcaccgcctg gccctgagag     360
agttgcagca agcggtccac gctggtttgc cccagcaggc gaaaatcctg tttgatggtg     420
gttccgaaat cggcaaaatc ccttataaat caaagaata gcccgagata gggttgagtg     480
ttgttccagt ttggaacaag agtccactat taaagaacgt ggactccaac gtcaaagggc     540
gaaaaaccgt ctatcaggc gatggccact acgtgaacca tcaccaaatc aagttttttg     600
gggtcgaggt gccgtaagca ctaaatcgga acctaaaggg agccccgatt tagagcttta     660
ctgggaaatc cgtcgaacgt gcgagaagca gttaaagcga aagacgggcc taaggctcaa     720
tttacgtcac tggcgtaaac acaaccgcgc cttatgcccc taaaaggcgt taaatggttc     780
ttaagaaaat tattgtctgt tgatgacggt naaancggct ttagtttaag agttcattng     840
nttttatgcc aaggtcgana agttttattt ancgacaaag agtagagtga gagngtggga     900
tgtgganggt gagtggagtg ngagtagtgn cggngatggc ggagagtagg tacgagtggg     960
```

```
agggtgtgg gacggtgtag atgggnggtg aggcagggct gggaggtgtg ngagggtagg      1020
gtgaggnngg cggggtgtag gggtgtgngt ggnacagagc ggatggngg                 1069

<210> SEQ ID NO 2
<211> LENGTH: 12
<212> TYPE: DNA
<213> ORGANISM: Bacteriophage M13mp18

<400> SEQUENCE: 2
ccacgctggt tt                                                         12

<210> SEQ ID NO 3
<211> LENGTH: 12
<212> TYPE: DNA
<213> ORGANISM: Bacteriophage M13mp18

<400> SEQUENCE: 3
tccacctggt tt                                                         12

<210> SEQ ID NO 4
<211> LENGTH: 13
<212> TYPE: DNA
<213> ORGANISM: Bacteriophage M13mp18

<400> SEQUENCE: 4
tccacgctgg ttt                                                        13

<210> SEQ ID NO 5
<211> LENGTH: 13
<212> TYPE: DNA
<213> ORGANISM: Bacteriophage M13mp18

<400> SEQUENCE: 5
tccacgctgg ttt                                                        13
```

METHODS AND FORMULATIONS FOR THE SEPARATION OF BIOLOGICAL MACROMOLECULES

RELATED PATENT APPLICATIONS

The instant application claims the benefit under 35 U.S.C. §119(e) to U.S. provisional application Ser. No. 60/107,798, filed on Nov. 10, 1998.

FIELD OF THE INVENTION

The present invention relates generally to methods and formulations for the separation of biological macromolecules, and in particular, to the separation to single-stranded DNA fragments according to their size using capillary electrophoresis with improved polyacrylamide matrixes.

BACKGROUND OF THE INVENTION

Capillary electrophoresis (CE) has demonstrated its advantages over standard slab gel based electrophoretic techniques as a rapid, high-throughput and high-resolution method for separation of biological macromolecules, such as proteins, peptides and nucleic acids (see e.g. Slater et al., Electrophoresis, 1998. 19(10), 1525–1541.) Capillary gel electrophoresis (CGE) is the CE-analog of traditional slab-gel electrophoresis and is most often used for size-based separation of biological macromolecules such as oligonucleotides, DNA restriction fragments and proteins. The separation is performed by filling the capillary with a sieving matrix, for example, cross-linked polyacrylamide, agarose or linear polymer solutions. The main advantages over slab-gel electrophoresis are a wider range of gel matrixes and compositions, on-line detection, improved quantitation and automation.

One of the major technological improvements in CE for DNA analysis was the introduction of replaceable polymer solutions as sieving matrixes (see, e.g., Sudor et al. Electrophoresis, 1991. 12:1056–1058; Ruiz-Martinez et al., Analytical Chemistry, 1993. 65(20):2851–2858.) The use of solutions of non-cross-linked synthetic or natural polymers has significantly increased the number of analyses per capillary column. Replacing the matrixes after each separation run creates reproducible analytical conditions. Another advantage of non cross-linked polymers is that they can be polymerized under controlled conditions in aqueous solutions, characterized, purified and stored indefinitely as dry powder (see, e.g., Goetzinger et al., Electrophoresis, 1998. 19(2):242–248.)

Solutions of polymers may then be prepared using various background electrolyte systems according to the requirements of a particular application. The versatility gained by the use of such entangled polymer solutions allows for a wide range of electrophoresis conditions to be utilized, such as elevated capillary temperature, without damaging the matrix structure (see, e.g., Kleparnik et al., Electrophoresis, 1996. 17(12):1860–1866). In contrast cross-linked gels are usually polymerized in situ under less than ideal conditions. Typically, these polymers are not fully characterized, and their quality varies from run-to-run. Cross-linked gel filled capillaries are also very prone to bubble formation due to temperature or osmotic stress. Additionally, replacement requires arduous removal, scrupulous clean up of the old material.

DNA separation applications (e.g. DNA sequencing, short tandem repeat [STR] analysis, differential display) traditionally performed using cross-linked polyacrylamide slab gels require both high resolving power (1 base resolution up to at least 500 bases) and strong denaturing capacity. This also applies for analogous applications using CE with replaceable polymer matrixes. Although replaceable linear polyacrylamide has been shown to provide unsurpassed separation efficiencies (see, e.g., Pariat et al., Journal of Chromatography, 1993. 652(1):57–66), it also exhibits sequence-specific anomalous migration of both double-stranded and single-stranded DNA (see, e.g., Berka et al., Electrophoresis, 1995. 16(3):377–388 and Wenz, Nucleic Acids Research, 1994. 22(19):4002–4008). Even under denaturing conditions (typically 6–8 M urea in the running buffer) anomalous migration of specific ssDNA fragments poses a serious problem causing compressions in DNA sequencing and low accuracy of DNA fragment sizing in genotyping applications. Thus, the secondary structure of single stranded DNA fragments can adversely affect the migration of DNA fragments in polymer solutions resulting in inaccurate sizing. In the area of DNA sequencing, the same secondary interaction of DNA fragments results in compressions that do not allow proper identification of the fragment sequence.

SUMMARY OF THE INVENTION

This invention discloses methods of biological macromolecule separation and formulations for linear polymer separation matrixes exhibiting improved DNA denaturation properties for use in capillary array electrophoresis. In a preferred embodiment, a combination of urea with organic denaturants (preferably 2-pyrrolidinone, N,N'-dimethylacetamide, and N,N'-dimethylformamide) resulted in a chemical environment strongly disfavoring base pairing of nucleic acids. Separation of single-stranded DNA fragments in these matrixes minimizes effects of DNA strand secondary structures on fragment mobility's, thus greatly improving the size-dependent separation. Further, this invention discloses optimized background electrolyte concentration and run voltage to further improve size-dependent migration of DNA fragments, in addition to enhanced denaturing properties of polymer matrixes. Biological applications of capillary electrophoresis such as differential display of mRNA, dideoxyfingerprinting, STR sizing and DNA sequencing would strongly benefit from using such formulations.

BRIEF DESCRIPTION OF THE DRAWINGS

FIG. 9: is a chart showing precision data.

DETAILED DESCRIPTION OF THE INVENTION

Figure 1:
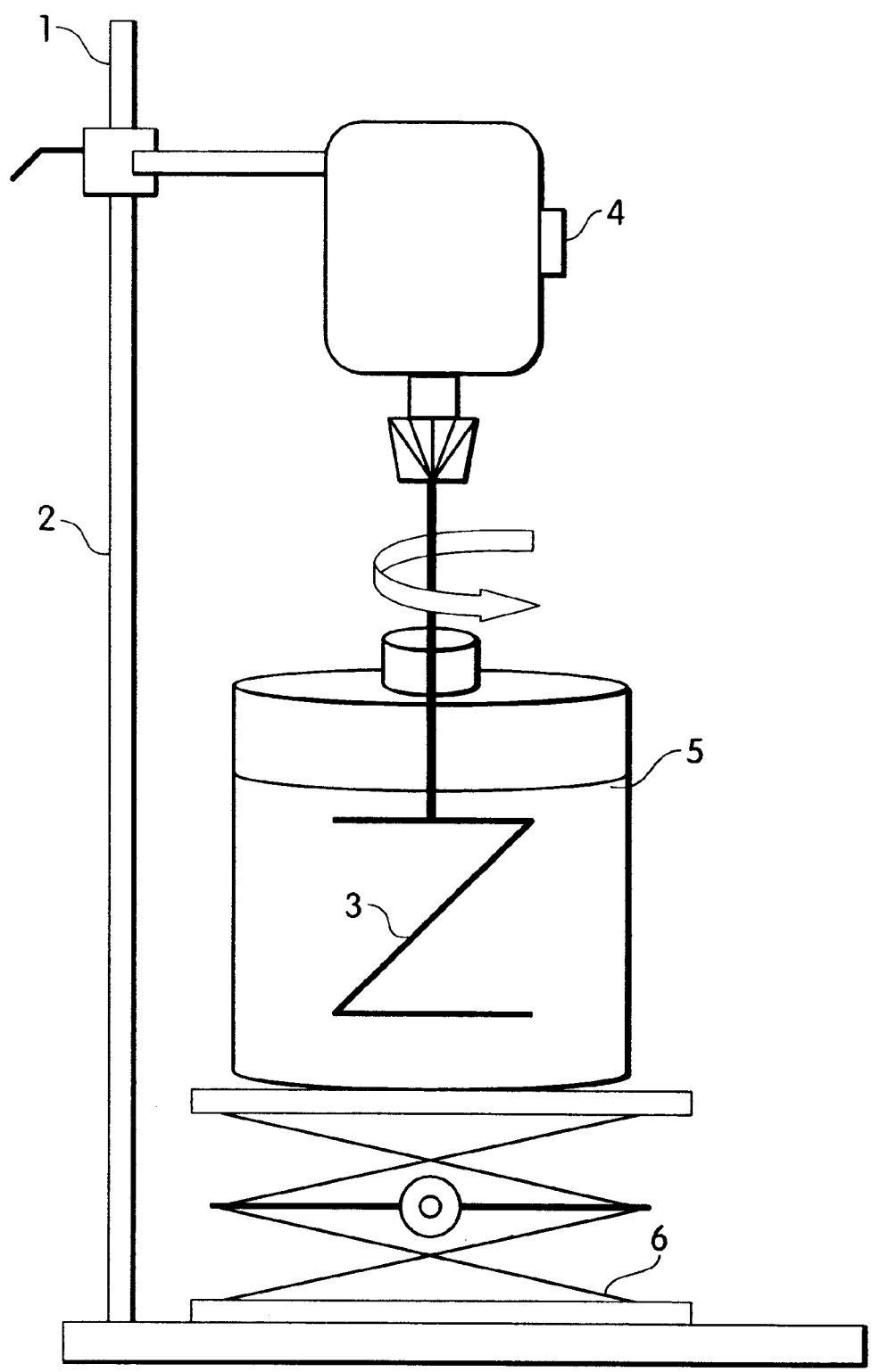
FIG. 1: A schematic representation of the device used for mixing the sieving matrix in quantities larger than 30 ml. (1) A clamp is used to support (2) an Heidolph high torque over-head stirrer (4) which was operated at 45xrpm. The matrix was placed in a glass (Pyrex) reactor (5) with a volume between 0.5–2.0 l. The stirrer was provided with a Z-shaped paddle (3) which allowed for the matrix to mix uniformly and a vacuum adapter to minimize evaporation of the sieving matrix. The reactor was set at the appropriate height for mixing using an adjustable lab-jacket (6). The entire assembly was then placed in a refrigerator set at 4° C. The matrices were stirred between 24–48 hrs.

The advent of automated capillary array instruments using replaceable polymer solutions as separation matrixes has greatly enhanced the throughput for DNA analysis. There are three main requirements for these polymer solutions to be used for sieving DNA fragments in automated capillary array systems: (i) enhanced denaturing capacity, (ii) adequate resolution, and (iii) sufficiently low viscosity (to allow facile replacement from the capillary columns). A linear polyacrylamide has been shown to provide the highest resolution observed for single stranded DNA fragments (see e.g., Current Opinion in Biotechnology, 1997. 8(1):82–93).

The main prerequisite for reliable and accurate size determination of an unknown analyte is comparing the mobility of any given unknown fragment with the mobility of internal standards separated in the same capillary. The use of internal standards for DNA analysis has been facilitated by multiple color fluorescence detection. The accuracy of size determination of an unknown analyte depends on the linear relationship between DNA fragment size and electrophoretic mobility. If either sizing standard peaks or DNA fragments to be sized exhibit aberrant electrophoretic mobility's, incorrect size determinations will result. Sequence-dependent anomalous mobility of double-stranded DNA fragments is a well-known phenomenon, which reflects functionally important DNA topologies (see, e.g., Berka et al., Electrophoresis, 1995. 16(3):377–388; Atha, Electrophoresis, 1998, 19(8–9):1428–1435). Sizing accuracy of DNA fragments can be greatly improved by separation of DNA fragments in their single-stranded forms under strong denaturing conditions. However, residual anomalous migration of one or more single-stranded fragments is usually attributed to sequence context secondary structures such as intrastrand base pairing (see e.g., Rosenblum et al., Nucleic Acids Research, 1997. 25(19) :3925–3929).

Nevertheless, commercially available polymer solutions do not provide sufficient denaturing capacity to eliminate non-specific size migration of DNA in capillary electrophoresis. In CE, two basic ways of increasing separation denaturing capacity are (i) adding chemicals known to denature DNA into the running buffer, and (ii) increasing column temperature. Ideally, chemical denaturants should be stable, non-hazardous and should not affect the sieving properties of the polymer matrix. Increasing column temperature above 40–60° C. may cause some technical difficulties especially for capillary array instruments. Urea has been used as the most common denaturant for ssDNA separations in concentrations up to 8 M, however, it does not provide for complete denaturing of some difficult sequencing compressions and size-dependent migration of some ssDNA sizing standards (see, e.g., Kleparnik supra; and Rosenblum supra.) Formamide is often used in addition to urea both in slab gel and CE separations of ssDNA in order to create strong denaturing conditions (see, e.g., Ruiz-Martinez, supra). Although it decreases the viscosity of polymer matrixes, thereby making them easier to replace into capillaries, formamide is toxic and unstable, decomposes rapidly into charged species at elevated temperature and decreases the lifetime of capillary coatings. The use of a less harmful cyclic compound, 2-pyrrolidinone, has been recently shown to improve sizing accuracy of GeneScan™ 500 (PE Applied Biosystems, Foster City, Calif.) standard in capillary electrophoresis using POP matrixes (see, e.g., Rosenblum et al., Nucleic Acids Research, 1997. 25(19) :3925–3929).

Several factors which affect denaturation of single stranded DNA fragments were optimized in the present invention: buffer concentration, organic denaturant concentration, polymer concentration, and capillary column temperatures. The Molecular Dynamics MegaBACE 1000 capillary array instrument utilized in this invention is capable of operating at a maximum of 44° C., due to hardware and optics stability issues. In order to alleviate the limitations in media denaturation capability we have investigated combinations of denaturants that would yield high denaturation of DNA without the need of using column temperatures above 45° C. Amides are among many chemical compounds that have been shown to denature double stranded DNA (see, e.g., Levine et al., Biochemistry, 1963. 2(1):168–175). Denaturing effectiveness of amides increases with lengthening of the alkyl chain as well as with substitution of methyl or ethyl groups on the nitrogen atom (see, e.g., Levine et al., supra). Although double stranded DNA denatures preferably at low ionic strength buffers, most standard electrophoresis buffer systems are designed at about 0.1 M concentration in order to reduce the risk of overheating due to Joule heat generation. CE, due to its excellent intrinsic Joule heat dissipation properties, may utilize buffers with reduced ionic strength, thereby further improving denaturing properties of a particular replaceable matrix/denaturant system.

We have based all matrix formulations used in the present invention on a linear polyacrylamide which has been shown to provide the highest resolution observed for single stranded DNA fragments (see, e.g., Quesada supra.).

Matrix Formulations

The formulations in this invention contain a high concentration of organic denaturants in a linear polyacrylamide solution to obtain high resolution and enhanced denaturation of single stranded DNA fragments. In a specific embodiment, the preferred formulations should include linear polyacrylamide (1–3% w/w) and organic additives such as, for example, (i) 2-pyrrolidinone, (ii) N',N'-dimethylformamide, and (iii) N',N'-dimethylacetamide at 5–40% (w/w) in combination with 3–8 M urea (preferred composition contains 6 M urea), with buffer concentrations between 0.1–300 mM TAPS-Tris-EDTA. Table 1 summarizes the composition of matrixes used in this invention.

Figure 2:
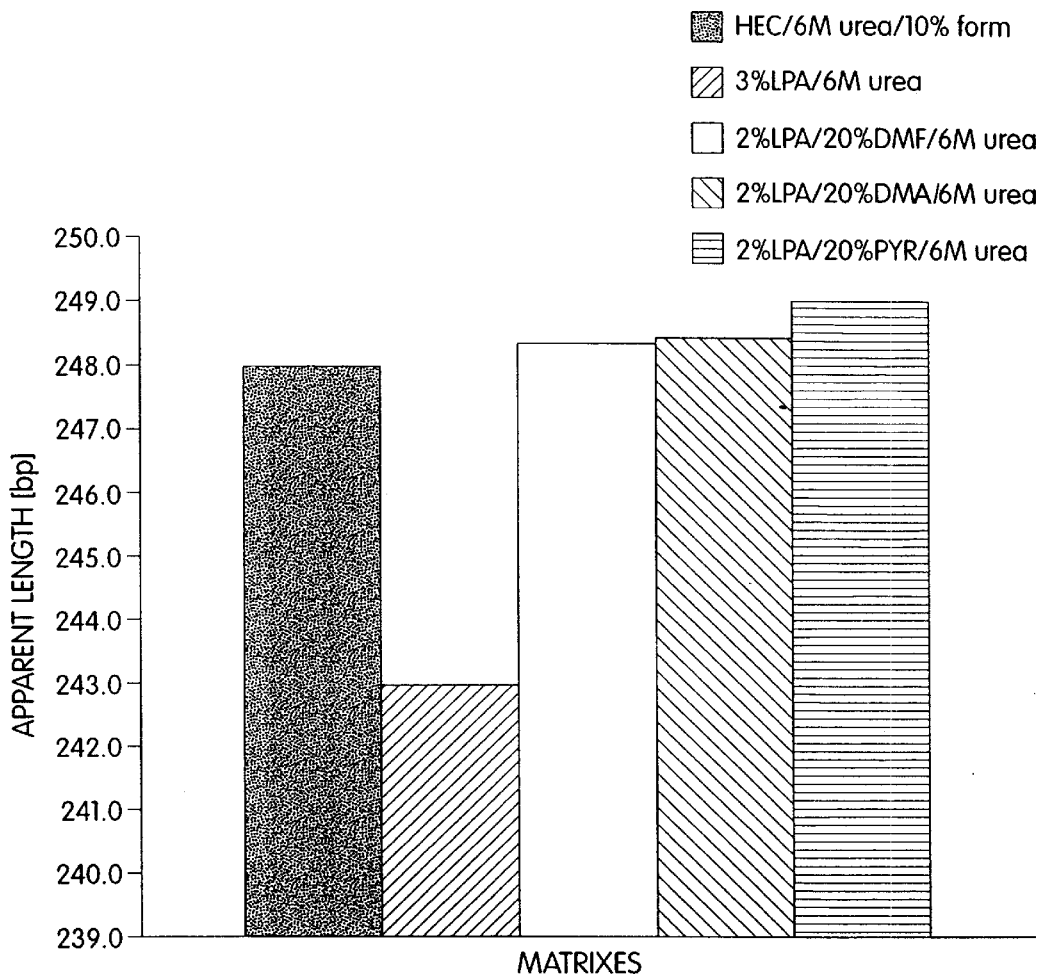
FIG. 2: The apparent lengths of the ROX GeneScan 250 bp fragment sized relative to FAM-labeled *Haemophilus influenzae* DNA restriction digest sample on the MegaBACE 1000 instrument using various replaceable separation matrixes. Conditions: sample injection 20 s/10 kV from deionized formamide; run voltage 12 kV, capillary temperature 44° C., running buffer 30 mM Tris, 100 mM TAPS, 1 mM EDTA pH 8.3.

Research, 1997. 25(19):3925–3929). The apparent size of the 250 base fragment obtained from the calibration using the H. influenzae digest was used as a measurement of the denaturing capacity of the media. FIG. 2 shows the relative size determined for the 250 base fragment in various formulations of this invention and compares it with commercially available matrix formulations. The apparent length of the 250 bp fragment is 243 bp when electrophoresed in the 3% linear polyacrylamide matrix with only 6 M urea as a denaturant. Addition of a second organic denaturing agent along with the 6 M urea in the matrix buffer affects the apparent length of the 250 bp fragment in a positive way, i.e., making its apparent length closer to the theoretical value of 250 bp. Particularly, 2-pyrrolidinone at 20% (w/w) concentration corrects the anomalous mobility of this fragment by 6 bp as compared to 3% LPA; 6 M urea matrix. The other two amides used, N',N'-dimethylformamide, and N',N'-

TABLE 1

Matrixes Used in the Invention

| Matrix | Linear poly-acrylamide (% w/w) | Denaturant composition | Buffer Composition |
|---|---|---|---|
| MegaBACE Gel Matrix (HEC) (Amersham/Pharmacia) | — | 6M urea, 10% (w/w) formamide | 30 mM Tris: 100 mM TAPS: 1 mM EDTA |
| MegaBACE ™ Long read matrix (Amersham/Pharmacia) | 3% | 6M urea | 30 mM Tris: 100 mM TAPS: 1 mM EDTA |
| LPA formulation LPA-PYR | 2.0% | 6M urea, 20% (w/w) 2-pyrrolidinone | 30 mM Tris: 100 mM TAPS: 1 mM EDTA |
| LPA formulation LPA-DMA | 2.0% | 6M urea, 20% (w/w) N',N'-dimethylacetamide | 30 mM Tris: 100 mM TAPS: 1 mM EDTA |
| LPA formulation LPA-DMF | 2.0% | 6M urea, 20% (w/w) N', N'-dimethylformamide | 30 mM Tris: 100 mM TAPS: 1 mM EDTA |

Preparation of the Matrix Formulations (FIG. 1)

FIG. 1 shows the schematic drawing of a matrix mixing device used in this invention. The preparation of the matrix formulations is described in detail in the EXAMPLES section of this invention.

Effect of Various Denaturants on Aberrant Mobility's of ROX GeneScan Ladder Peaks (FIG. 2)

The restriction enzyme digest products from H. influenzae genomic DNA were used as a standard in order to determine a relative size of 250 bp and 340 bp fragments from the GeneScan™ ROX 500 ladder (Applied Biosystems, Foster City, Calif.)(see FIG. 2). The expected fragments from the enzymatic digest are known since the genome of H. influenzae has been completely sequenced and is a publicly available sequence (see, e.g., Fleischmann et al., Science, 1995. 269:496–512). A base to frame conversion algorithm was produced using the theoretical size of the peaks generated from the H. influenzae digest and the migration time (in frames) of the peaks on the electropherogram. Using this scale the size for the GeneScan™ ROX 500 fragments was determined. From the literature it is known that the fragments 250 and 340 bases in length of the GeneScan™ ROX 500 ladder do not exhibit a linear relationship between their electrophoretic mobility and theoretical length and migrate anomalously fast (see, e.g., Rosenblum et al., Nucleic Acids dimethylacetamide, are highly effective as denaturants as well, resulting in apparent lengths of 248.3 and 248.4 bp, respectively. The 250 bp fragment sizes as 248 bp when run using a 10% formamide containing hydroxyethylcellulose matrix. Formamide has been shown to improve DNA sequencing compressions in concentration of up to 30% in LPA matrixes for capillary electrophoresis (see, e.g., Ruiz-Martinez et al., Analytical Chemistry, 1993. 65(20):2851–2858), however, formamide containing matrixes are highly unstable at room temperature or elevated column temperatures due to decomposition and also decrease the lifetime of capillary coatings. The comparison of matrixes in FIG. 2 may also reflect different properties of the two polymers (HEC vs. LPA) and their concentrations.

Figure 3:
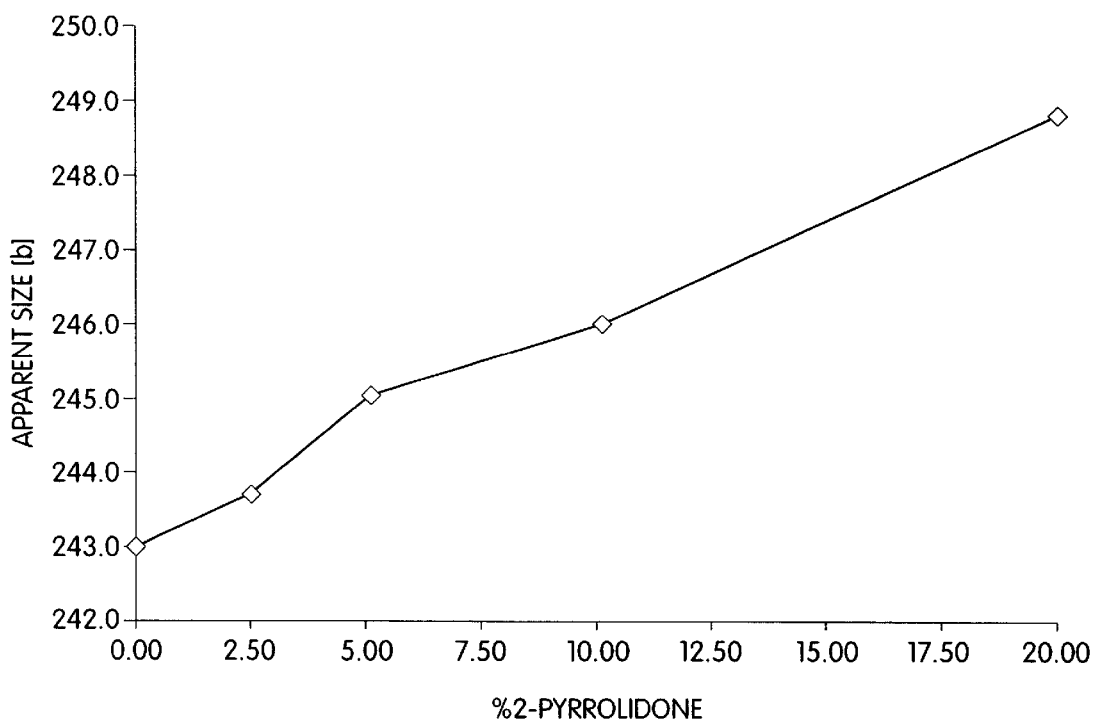
FIG. 3: The apparent lengths of the ROX GeneScan 250 bp fragment sized relative to FAM-labeled *Haemophilus influenzae* DNA restriction digest sample on the MegaBACE 1000 instrument using increasing concentrations of 2-pyrrolidinone. Conditions: sample injection 20 s/10 kV from deionized formamide; run voltage 12 kV, capillary temperature 44° C., running buffer 30 mM Tris, 100 mM TAPS, 1 mM EDTA pH 8.3.
Figure 4:
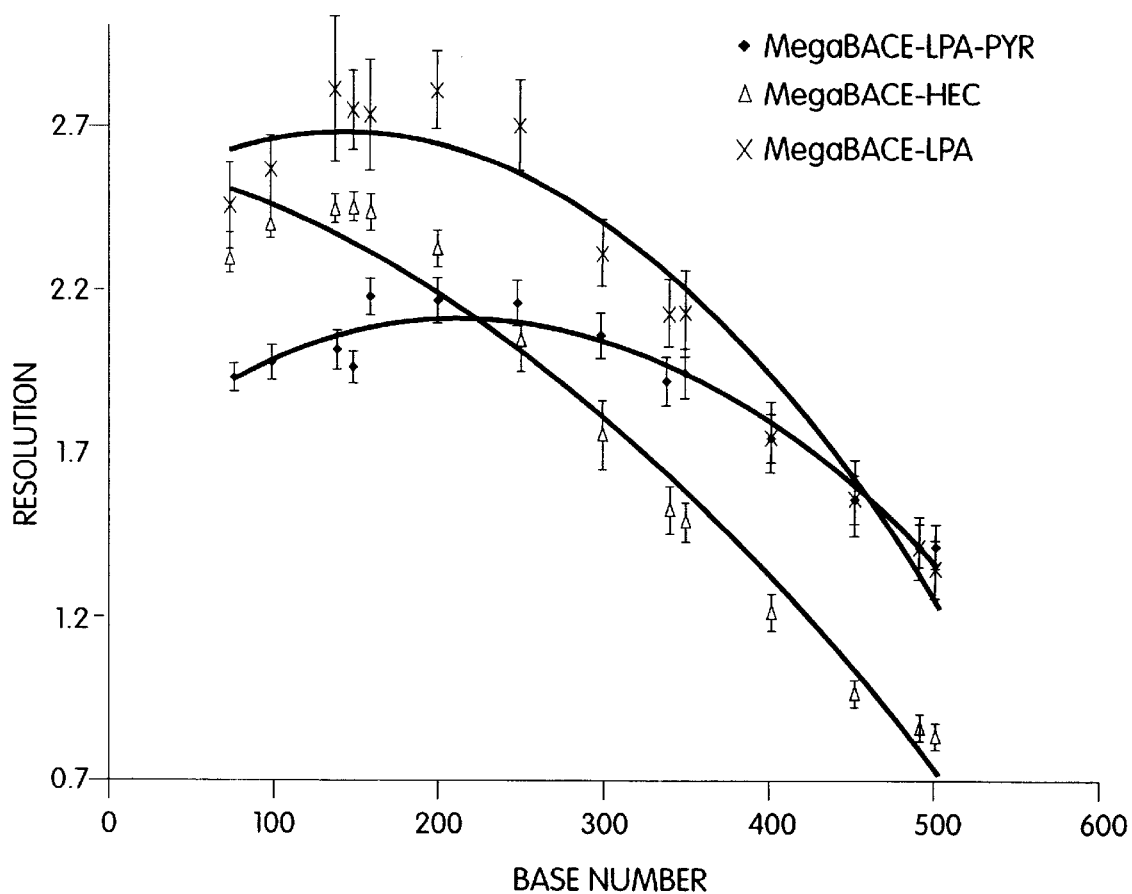
FIG. 4: The resolution of the GeneScan 500 ROX peaks 75 to 500 bases using three types of replaceable polymer matrixes—commercially available (i) hydroxyethylcellulose ("MegaBACE-HEC", represented by a cross), (ii) MegaBACE Long Read Matrix ("MegaBACE-LPA", represented by a cross), and (iii) a 2% LPA containing 20% 2-pyrrolidinone ("MegaBACE-LPA-PYR", represented by a diamond). Electrophoretic conditions were the same as in FIG. 1.

Effect of 2-pyrrolidinone Concentration on Anomalous Migration of ROX GeneScan 500 Ladder Peaks (FIG. 3; FIG. 4)

2-pyrrolidinone has been chosen as the most effective denaturant for more detailed investigation since the most positive tendency was observed on migration of ROX 250 bp fragment. In order to find the optimum denaturing composition, the concentration of 2-pyrrolidinone in a separation matrix was varied from 5% to 20%, while keeping the urea concentration constant at 6 M. Increasing the urea concentration above 6 M is not practical due to its limited solubility. On the other hand, up to 20% (weight) of 2-pyrrolidinone could be mixed into the starting 3% LPA solution, resulting in 2% LPA concentration and allowing for background electrolyte concentration compensation of 100 mM TAPS; 30 mM Tris; 1 mM EDTA. The plot in FIG. 3 shows nearly linear relationship between 2-pyrrolidinone concentration and apparent size of the ROX 250 bp fragment. Apparent size closest to its theoretical size (248.8 b) was obtained at 20% concentration of 2-pyrrolidinone. Higher denaturant concentrations would have diluted the LPA concentration below 2% and would have adversely affected the resolution for fragments below 100 bp. In accordance with the literature data, addition of 2-pyrrolidinone in the separation matrix increases the electrophoresis time by roughly 30% per each 10% of the denaturant while keeping all other parameters constant (see, e.g., Rosenblum et al., Nucleic Acids Research, 1997. 25(19):3925–3929). We were able to compensate for this effect by increasing the run voltage from 10 kV to 12 kV in our system which led to separation of fragments 500 bp in length in about 65 minutes without any significant loss of resolution in that size range. FIG. 4 presents a plot of resolution versus fragment length for three sieving matrices including: two commercially available: LPA (Amhersham-Pharmacia) HEC (Amhersham-Pharmacia) and the embodiment formulation (containing 20% 2-pyrrolidinone). From this figure, it can be observed that the 2% LPA matrix containing 20% 2-pyrrolidinone exhibits superior resolution to the commercial LPA matrix in the region beyond 450 bp while maintaining resolution >2.0 between 100 and 350 bases, more than sufficient to obtain reliable sequence reads or fragment analysis data.

Figure 5:
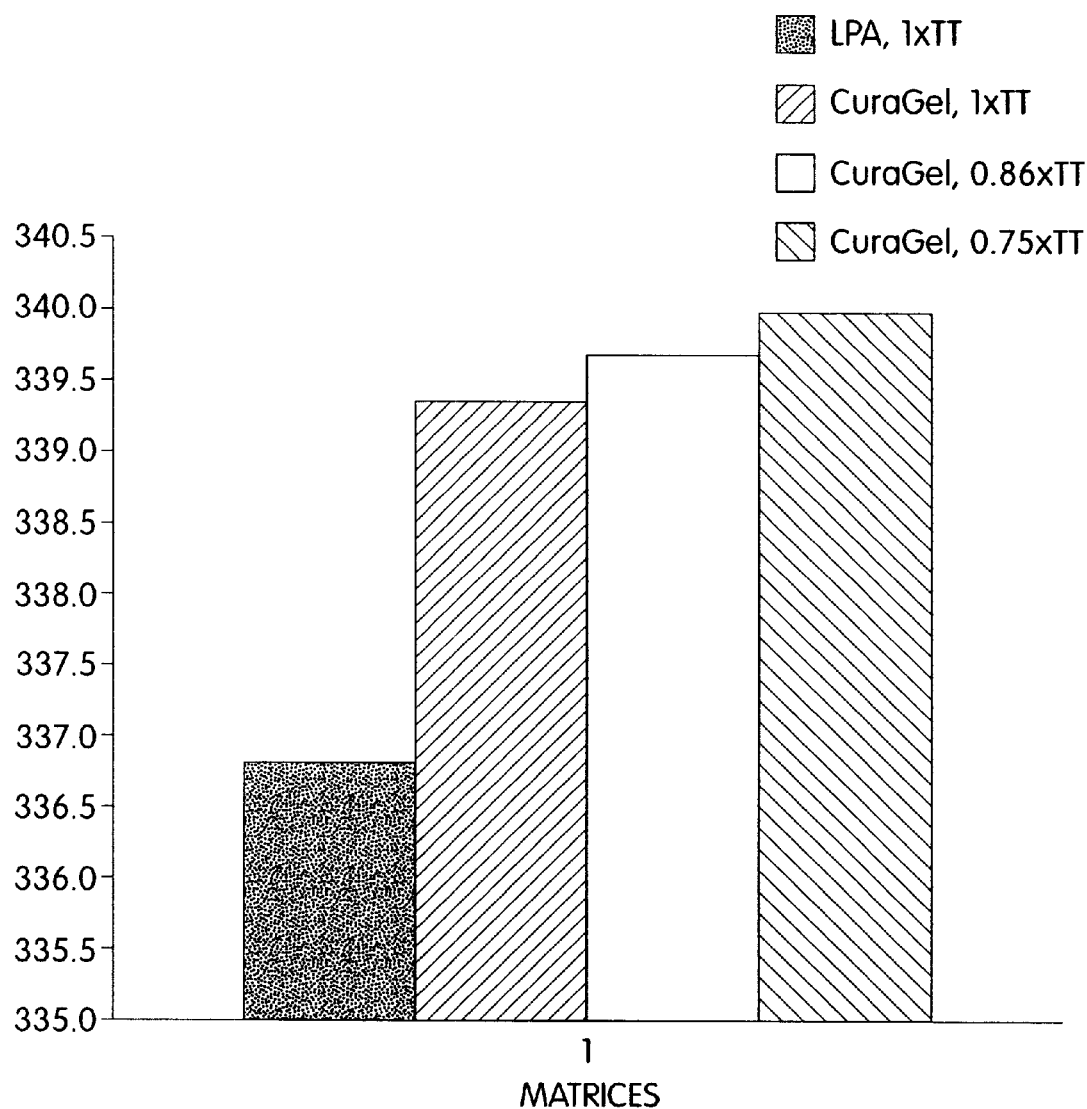
FIG. 5: The apparent lengths of the ROX GeneScan 340 bp fragment sized relative to FAM-labeled *Haemophilus influenzae* DNA restriction digest sample on the MegaBACE 1000 instrument using various concentrations of Tris/TAPS/EDTA background electrolyte. Electrophoretic conditions were the same as in FIG. 1.

Effects of Running Buffer Concentration on Anomalous Migration of ROX GeneScan 500 Ladder Peaks (FIG. 5)

Although it is known that double stranded DNA denatures preferably at low ionic strength buffers, most standard electrophoresis buffer systems are designed at about 0.1 M concentration to reduce the risk of overheating due to Joule heat generation (see, e.g., Hames & Higgins, Nucleic Acid Hybridization: A Practical Approach. 1985; IRL Press, Oxford and Washington D.C.). Capillary electrophoresis, because of its excellent intrinsic Joule heat dissipation properties, may utilize buffers with reduced ionic strength thereby further improving denaturing properties of a particular replaceable matrix/denaturants system. To examine effects of reduced ionic strength electrophoresis buffer on anomalous migration of the ROX GeneScan 500 ladder fragments, separation matrixes were prepared with a background electrolyte concentrations 1× (30 mM Tris, 100 mM TAPS, 1 mM EDTA), 0.86× (26 mM Tris, 86 mM TAPS, 0.86 mM EDTA), 0.75× (22.5 mM Tris, 75 mM TAPS, 0.75 mM EDTA), and 0.66× (19.8 mM Tris, 67 mM TAPS, 0.67 mM EDTA). With decreasing background electrolyte concentration, the ROX 340 bp fragment migrated closer to its theoretical size, as shown in FIG. 5. The background electrolyte concentration of 0.66× (19.8 mM Tris, 67 mM TAPS, 0.67 mM EDTA) has been chosen for subsequent experiments.

Figure 6:
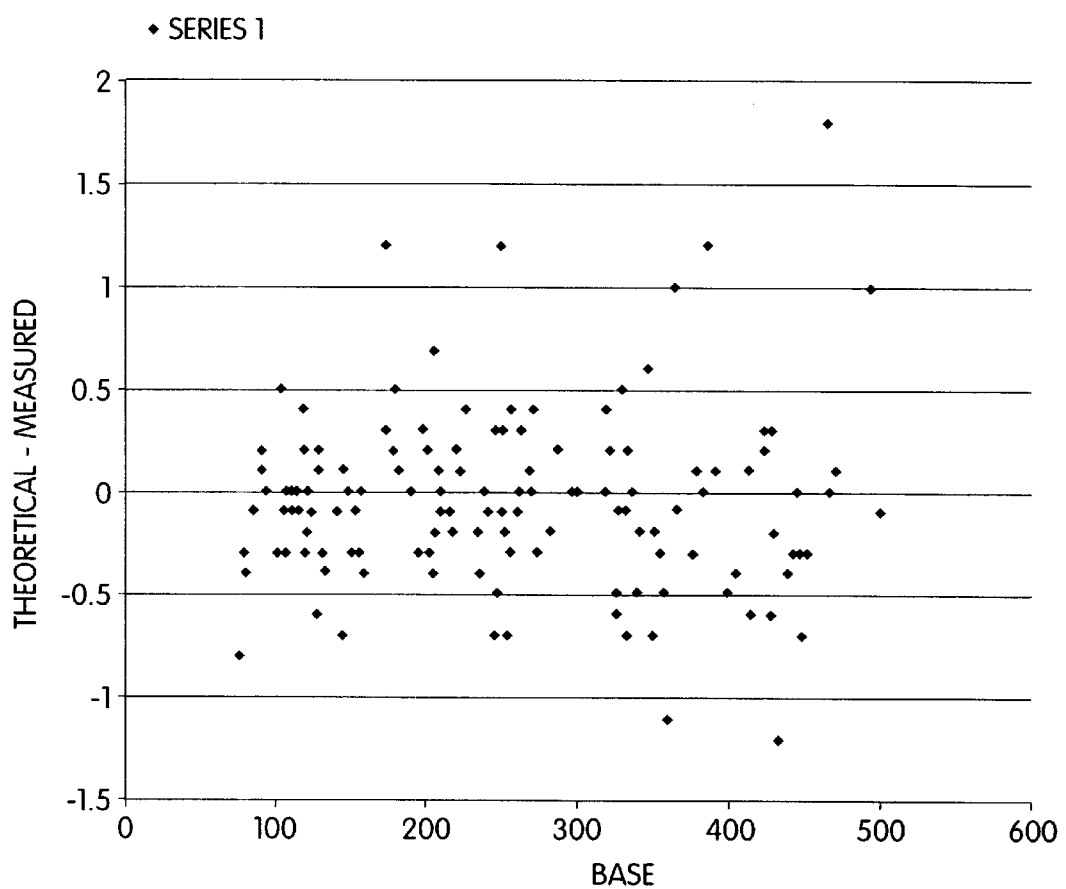
FIG. 6: The accuracy after calibration. Data are included from *H. influenzae* i0m0, m1c0, mli0 and m0p0.

Accuracy and Precision of DNA Fragment Size Determination Using Matrixes With Improved Denaturing Capabilities (FIG. 6)

Analysis of short tandem repeat (STR) markers is one of biological applications that have attracted a considerable attention in the field of capillary electrophoresis. STR polymorphism profiling requires single base resolution separations up to 400 bases, high sizing accuracy and precision. Sizing accuracy values reported in the literature using a capillary electrophoresis instruments were found to be 0.1–0.2 bp (within run) and between 0.2 to 0.8 bp (run-to-run) (see, e.g., Vainer et al., Genomics, 1997. 41(1):1–9; Deforce et al., Journal of Chromatography, 1998. 806(1) :149–155; Lazaruk et al., Electrophoresis, 1998. 19(1) :86–93; Mansfield et al., Electrophoresis, 1998. 19(1) :101–7; Wenz et al., Genome Research, 1998. 8(1):69–80; Dimosimonin et al., Electrophoresis, 1998. 19(2):256–261). The use of an elevated capillary column temperature (60° C.) was found to improve sizing precision, to increase the lifetime of capillaries, as well as reduced electrophoresis time (Isenberg et al., Electrophoresis, 1998. 19(1):94–100). These results are in agreement with previously published data on DNA sequencing by capillary electrophoresis at high column temperature (see, e.g., Kleparnik et al., Electrophoresis, 1996. 17(12):1860–1866). It is thus evident that DNA sequencing and sizing applications could benefit from severe denaturing conditions, such as combination of chemical denaturants and temperatures above 60° C. However, some deviations from a strict size-dependent DNA migration may still exist under these conditions and further increase in denaturing capacity of a separation matrix would be desirable.

In this invention, GeneScan 500 ROX ladder peaks were size-calibrated as described in the EXAMPLES. Sizing accuracy is theoretical size minus measured size (after calibration) where the measured size is obtained from separation traces calibrated in base-pair units using *H. influenzae* (HI) digests. Results of sizing accuracy measurements are shown in FIG. 6. According to a statistical analysis of the data, the data fail a test for normality (Kolmogorov-Smimoff) with a K-S Dist.=0.111852 and a K-S Prob.= 0.000156. Nevertheless we can report the following statistics. The sample size is 143 with a median of −0.100. The maximum and minimum values are 1.8 and −1.2 respectively while the 25% and 75% range points are at −0.3 and 0.2 respectively. The 5% and 95% points are at −0.70 and 0.64 while the 1% and 99% points are at, respectively, −1.11 and 1.24. Sizing precision is better than 0.1 base on 24 capillaries of *H. influenzae* digest i0m0 from two separate runs; sixteen peaks were used for each trace.

Precision data are shown in FIG. 9.

Figure 7:
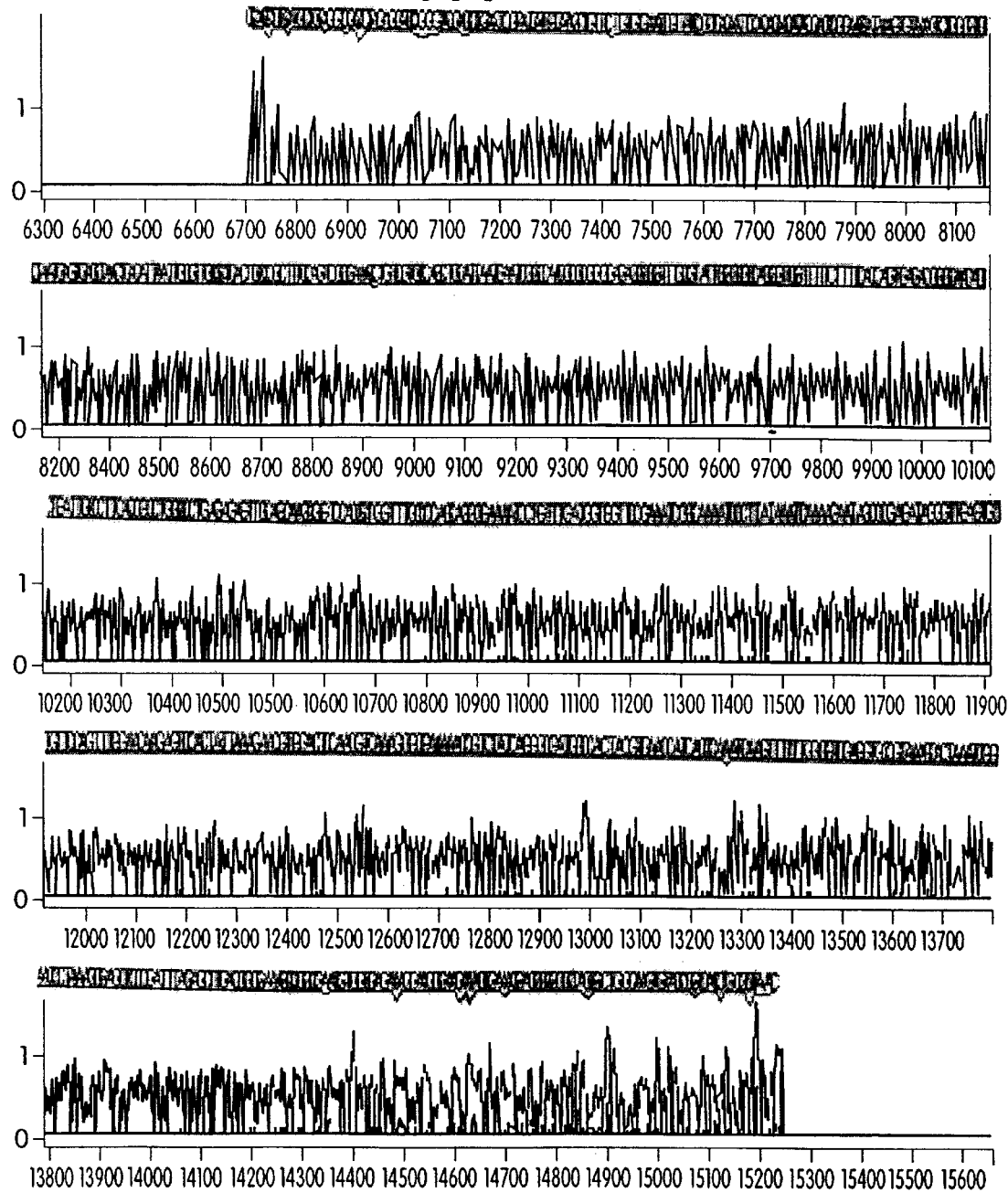
FIG. 7: Illustration of M13mp18 sequencing. Conditions: 2% (w/w) linear polyacrylamide:20% (w/w) 2-pyrrolidinone:6M urea:30 mM Tris:100 mM TAPS:1 mM EDTA at 44° C., matrix fill time 2 minutes, matrix equilibration 15 minutes prior to run, 5 min. pre-run. Samples injection for 20 s at 10 kV. The separation was performed at constant electric field at 10 kV.
Figure 8A:
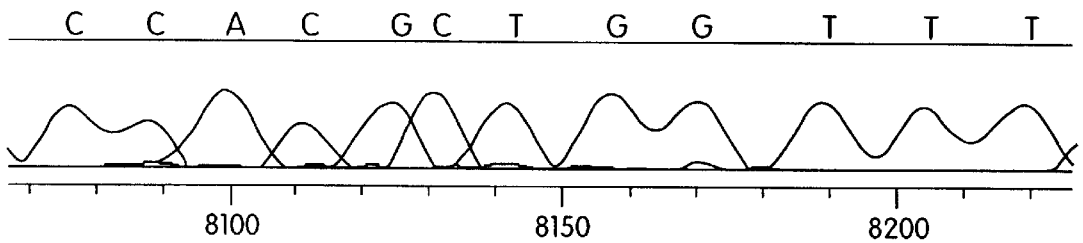
FIG. 8: The effect of matrix denaturants on resolution of the CGCT compression at 400 bases of the M13mp18 (–21) sequence using 1.5% HEC; 6M urea; 10% Formamide (A), 3% LPA; 6 M urea (B), 2% LPA; 6 M urea; 20% 2-pyrrolidinone (C), and 2% LPA; 6 M urea; 20% DMA (D).
Figure 8B:
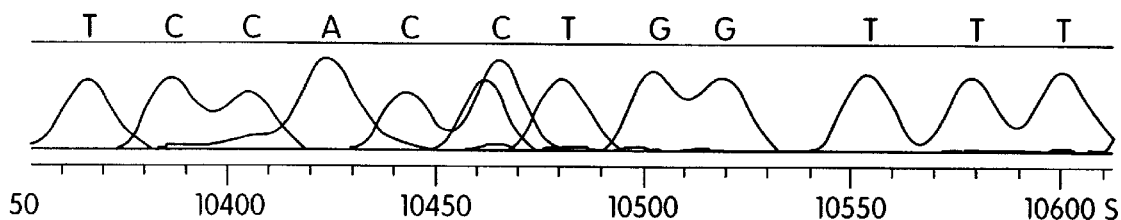
Figure 8C:
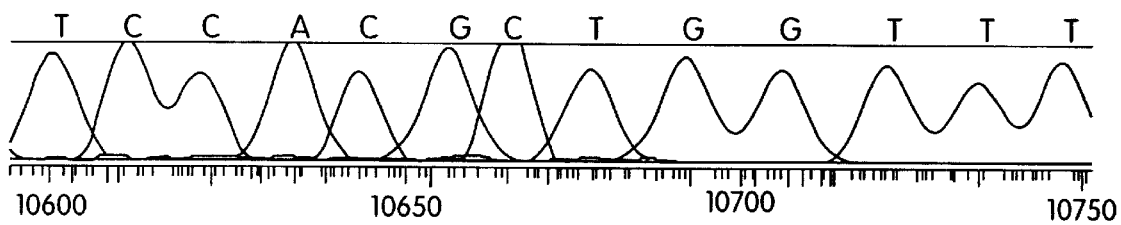
Figure 8D:
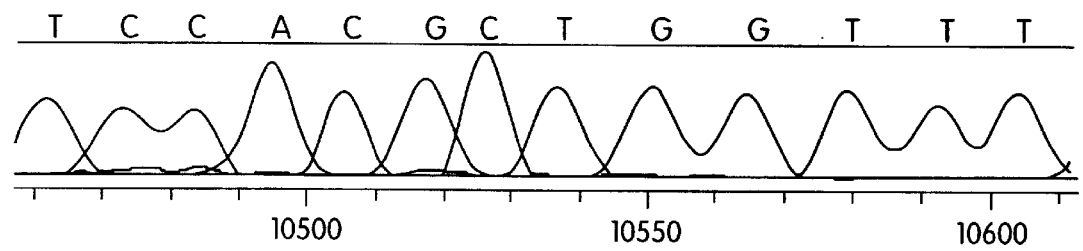

DNA Sequencing Using Matrixes With Improved Denaturing Capabilities (FIG. 7; FIG. 8)

Four different formulations were evaluated for DNA sequencing. For comparison, both the MegaBACE Long read matrix and HEC matrix™ (Amersham-Pharmacia) formulations were employed along with two inventive formulations. The first formulation contained 2% (w/w) linear polyacrylamide (MegaBACE Long read matrix), 20% (w/w) 2-pyrrolidinone: 6 M urea: 30 mM Tris:100 mM TAPS:1 mM EDTA and the second formulation contained 2% (w/w) linear polyacrylamide (MegaBACE Long read matrix), 20% (w/w) N',N'-dimethylacetamide: 6 M urea:30 mM Tris: 100 mM TAPS:1 mM EDTA. FIG. 7 shows the complete electropherogram for the separation of sequencing fragments on the 2% (w/w) linear polyacrylamide: 20% (w/w) 2-pyrrolidinone: 6M urea: 30 mM Tris:100 mM TAPS:1 mM EDTA at 44° C., the x axis display the migration time in data frames. The data acquisition rate for the MegaBACE was 1.8 Hertz. In FIG. 7 the called sequence of the fragment is displayed on top of the trace. According to the MegaBACE sequencing software this trace reads 719 bases with an accuracy of 99.1% versus the consensus M13mp18 sequence. There are a number of well known compressions in the sequence of M13 (see, e.g., Kleparnik et al., supra). FIG. 8 shows a portion of the electropherograms of the separation of M13 sequencing reaction products (around 400 bases) using the HEC and three different linear polyacrylamide formulations. In FIG. 8 the x-axis is in frames and the MegaBACE data acquisition rate is 1.8 hertz. The y-axis in FIG. 8 is arbitrary fluorescence units. As observed in FIG. 8 the separation of the CGCT stretch is strongly affected by the separation media. This region is a well known compression in the sequence of M13 around 400 bases (see, e.g., Kleparnik Supra.). It can be clearly observed in FIG. 8 that both the formulation with 2-pyrrolidinone and N', N'-dimethylacetamide can resolve the CGCT compression more readily that the commercially available formulations. It can also be observed that the spacing between fragments in the inventive formulations in FIG. 8 is more uniform than in the commercial matrixes. Such an improved resolution of compressed sequences, especially in GC-rich DNA templates will greatly improve base calling accuracy.

EXAMPLES

1. Samples

GeneScan-500 ROX standards were obtained from Perkin Elmer (Part No. 401734, Perkin Elmer, Applied Biosystems Division, Foster City, Calif.) and used in dilutions ranging from 1:20 to 1:100 in either deionized formamide or nanopure water for electrokinetic injection into capillaries. FAM-labeled fragment samples were prepared from *Haemophilus influenzae* genomic DNA by the QEA™ chemistry process as described elsewhere (see, e.g., U.S. Pat. No. 5,871,697). The sequencing samples were the MegaBACE™ sequencing standard (Amersham-Pharmacia) which contains 4 color M13 sequencing reaction generated with ThermoSequenase™ (Amersham-Pharmacia) DNA polymerase and M13 (−40) forward primers (Sambrook, et al., *Molecular Cloning: A Laboratory Manual*, 2nd ed., Vols. 1, 2 and 3. Vol. 1, 2, 3. 1989, Cold Spring Harbor, N.Y.: Cold Spring Harbor Laboratory Press. 1626) labeled with energy transfer dyes (Amersham-Pharmacia).

2. Electrophoresis Apparatus

MegaBACE 1000 DNA Sequencing System (Amersham-Molecular Dynamics, Sunnyvale, Calif.) was used in this invention. MegaBACE 1000 is a capillary array instrument utilizing 6 arrays of 16 capillaries, 100 $\mu$m I.D., 64 cm total length, 44 cm effective length. The instrument was operated at dual laser excitation mode (488 and 532 nm), FAM signals were detected in spectral channel 2 after a 520/20 band pass filter, ROX 1S signals were detected in channel 3 after passing through a 610/LP long pass filter. Data was acquired at the rate of 1.8 Hz. Electrophoresis conditions: run voltage 12 kV, capillary temperature 44° C., sample injection 20 s/10 kV.

3. Separation Matrix Preparation (FIG. 1)

The weight of a wide mouth (>1") glass jar (previously cleaned with deionized water) is obtained and set to zero. MegaBACE™ Long read matrix (Amersham-Pharmacia, Piscataway, N.J.) (provided in a 10 ml plastic syringe or one liter container) sufficient to prepare a 0.8–2.9% w/w solution was added to the jar. The weight of Long read™ (Amersham-Pharmacia) sieving matrix was recorded. A pre-determined amount of concentrated electrophoresis buffer was added to the glass vial to a final concentration between 10–50 mM Tris (preferred concentration 20 mM), 10–300 mM TAPS (preferred concentration 67 mM), 0.1–1.0 mM EDTA (preferred concentration 0.7 mM). Solid urea was also added to create a final concentration between 6–8 M (the most preferred concentration was 6 M). The maximum urea concentration is limited by its saturation level (~8 M). The organic denaturant was then added to a final concentration of 5–40% (w/w). The preferred denaturants include 2-pyrrolidinone, N',N'-dimethylacetamide, and N',N'-dimethylformamide. The most preferred denaturant combination was 20% 2-pyrrolidinone and 6 M urea. The solution was then brought to a final weight by the addition of deionized water. To the mix a ⅞" magnetic stirrer was added and the jar was capped and sealed using Para-film™. The solution was stirred at low speed on a magnetic stirrer at room temperature for about 12–18 hours prior to use. When the solution was completely dissolved, the mixture was withdrawn from the wide mouth jar using 10 cc plastic syringes. The plastic syringes containing the polymer solution were fitted with pipet tips and 0.75 ml of the mixture was dispensed into 2 ml screw cap vials. The solution was degassed by centrifuging (5,000×RPM) the tubes in a Speed-Vac concentrator without vacuum for 4 minutes. The tubes were subsequently closed with an o-ring cap and stored at 4° C.

Matrix preparation containing 20% of 2-pyrrolidinine was also scaled up to a production level as described below (see also FIG. 1): The procedure for preparation of the separation matrix was modified to mix quantities up to 1,000 g. The weight of a 2 liter Pyrex reactor (Corning, Corning, N.Y.; 5. in FIG. 1) was obtained and set to zero. To the Pyrex reactor 400.0 g of MegaBACE Long Read matrix (Amersham-Pharmacia, Piscataway, N.J.), 92.0 ml of 2-pyrrolidinone (Aldrich Chemical Company, Milwaukee, Wis.), 72.0 g of urea (Amresco, Solon, Ohio) were added and brought up to a final solution weight of 600 g with distilled water. The solution was mixed at 4° C. in a refrigerator using a Heidolph over-head stirrer at 45×RPM for 24–32 hours. The over-head stirrer was equipped with an Z-shaped blade (3. in FIG. 1) and a vacuum adapter (4. in FIG. 1) to minimize evaporation of the solution. The Z-shaped blade provided homogeneous mixing of the solution and minimized shearing of the high molecular weight polymers (see FIG. 1). After mixing, the separation matrix was dispensed into 12 oz. cartridge retainers (Norlico Corporation, Hampton Falls, N.H.). The retainers are placed on a barrel loader (Norlico Corp.) and used to fill 55 cc syringes with the separation matrix. The syringes are used on a 2000×L digital dispenser (Norlico Corp.) to dispense 1.5 ml of the matrix into 2 ml o-ring screw cap vials. The 2 ml vials containing the separation matrix were stored at 4° C. The vials were spun for 5 min at 5,000×rpm prior to filling of the capillary arrays on the MegaBACE instrument (Molecular Dynamics, Sunnyvale, Calif.).

4. Method of Measuring Apparent Length of ROX GeneScan Peaks

Several *H. influenzae* restriction digests were prepared and run on the MegaBACE instrument in order to obtain a sizing calibration for the GeneScan 500 ROX ladder fragments. The successful double digests included i0m0 (BglII/BspHI), mic0 (MfeI/Apa L1), mli0 (MfeI/BglII), and m0p0 (BspHI/BstYI). A Mathematica program was written that allowed for a precise determination of a peak of interest coordinates in frame number (x, or time axis) and signal strength (y, or relative fluorescence axis). The peak maximum frame number was used to obtain the sizing values for the MegaBACE runs. The GeneScan fragment effective sizes, accounting for mobility shift and electrophoretic mobility, were interpolated from a third order fit of *H. influenzae* p0r0. First, a preliminary calibration was obtained as follows. An association between frame number and *H. influenzae* i0m0 fragment size was obtained. Linear interpolation using four or five i0m0 peaks per ROX peak was used to obtain effective lengths of the ROX fragments, using the frame numbers of their peaks. Assignability of the *H. influenzae* p0r0 signal trace was checked, and found peaks could not be assigned with sufficient confidence to measure the accuracy. Upon checking the calibration, e.g. examining the *H. influenzae* i0m0 sizing, it was found that there were observable error trends. For example, all short fragments may have sized as too short while all long fragments may have sized as too long. Therefore, to obtain a more accurate sizing calibration the more dense (containing 58 fragments between 21 and 591 bp in size) *H. influenzae* mic0 digest was used for the primary calibration. A new assignment was obtained between frame number and fragment size using *H. influenzae*/mlc0. From four to eleven of the mlc0 peaks were used to obtain a linear interpolation for each ROX size. The number of peaks chosen for the linear fit was variable and chosen to include all peaks within a roughly +/−50 base window. The sizing of *H. influenzae* i0m0 and mic0 was again examined to check accuracy and see if any trends were present. We found that the bands seemed to size low between 100 and 139. This observed trend was confirmed, for example with *H. influenzae* mli0. Checking the entire mlc0 digest revealed that residual difference values (theoretical-measured) were all positive up to about 250 bases and that there were errors near 500 bases (and for values extrapolated to longer lengths). Using this information, corresponding adjustments were made to the calibration, for example: add 0.3 to each value up to 250. The sizing was checked and the values adjusted until better values (closer to zero) were obtained for (theoretical—measured). Next another digest (this time m0p0) was checked for the values of theoretical minus measured. In this case the accumulated difference of all (theoretical-measured) values was checked and found to be <0.1 base on average. Precision was determined by examining the size of identical fragments measured multiple times.

5. Software

OGI® was used to view data from all 96 capillaries. GeneScape®, an Internet based bioinformatics system was utilized for data analysis. Calculation of apparent fragment sizes based on standard peak mobility's, as well as calculations of resolution, efficiency, and selectivity were performed by a program written in Mathematica 3.0 (Wolfram Research, Champaign, Ill.). Sigma Stat (SPSS Inc., Chicago, Ill.) was used to perform statistical analysis on experimental data.

What is claimed is:

1. A replaceable matrix formulation comprising:
   (a) a linear polyacrylamide (LPA) solution, wherein the LPA concentration in said solution ranges between 1% to 3% (w/w);
   (b) at least one organic denaturant, wherein the organic denaturant is selected from the group consisting of: 2-pyrrolidinone, N',N'-dimethylacetamide and N',N'-dimethylformamide;
   (c) a buffer; and
   (d) 3 M to 8 M urea, wherein said formulation is capable of separating nucleic acids.

2. The matrix formulation according to claim 1, wherein the organic denaturant concentration ranges between 5%–20% (w/w).

3. A replaceable matrix formulation of claim 1, wherein the urea concentration is 6 M urea.

4. A replaceable matrix formulation of claim 1 comprising the following:
   (a) a linear polyacrylamide solution comprising 2% (w/w) of the matrix;
   (b) at least one denaturant, the organic denaturant comprising 20% (w/w) of the matrix;
   (c) a buffer comprising about 20 mM Trizma Base, 67 mM TAPS, 0.7 mM EDTA; and
   (d) 6 M urea.

5. The matrix formulation according to claim 1, wherein the organic denaturant concentration ranges between 5–40% (w/w).

6. The matrix formulation according to claim 1, wherein the organic denaturant is stable.

7. The matrix formulation according to claim 1, wherein the organic denaturant is non-hazardous.

8. A method of biomacromolecule separation using a capillary electrophoresis device comprising the matrix formulation according to claim 1 and a buffer.

9. The method according to claim 8, wherein the electrophoresis device is operated at a run voltage of between 10 kV–12 kV.

10. The method according to claim 8, wherein the electrophoresis device is operated at a run voltage of at least 12 kV.

11. The method according to claim 8, wherein the electrophoresis device is operated at temperature ranging between 40° C. and 60° C.

12. The method according to claim 11, wherein the electrophoresis device is operated at 44° C.

13. The method according to claim 8, wherein the buffer consists essentially of:
   (a) EDTA, with a concentration ranging between 0.6–1.0 mM;
   (b) Trizma Base, with a concentration ranging between 12–30 mM; and
   (c) TAPS, with a concentration ranging between 50–85 mM.

14. The method according to claim 8, wherein the biomacromolecule separation is used in nucleic acid sequencing.

15. The method according to claim 8, wherein the nucleic acid separation is used in the determination of the molecular size of a nucleic acid.

16. The method according to claim 8, wherein the nucleic acid separation is used in the differential display of messenger RNA (mRNA).

17. The method according to claim 8, wherein the nucleic acid separation is used in dideoxyfingerprinting.

18. The method according to claim 8, wherein the nucleic acid separation is used in short tandem repeat (STR) analysis.

19. The method according to claim 8, wherein the buffer comprises:

(a) EDTA, with a concentration ranging between 0.1–1.0 mM;

(b) Trizma Base, with a concentration ranging between 10–50 mM; and (c) TAPS, with a concentration ranging between 10–300 mM.

20. The method of claim 8, wherein the buffer comprises:

(a) 0.7 mM EDTA;

(b) 20 mM Trizma Base; and (c) 67 mM TAPS.

21. A replaceable matrix formulation comprising:

(a) a linear polyacrylamide (LPA) solution, wherein the LPA concentration in said solution ranges from 1% to 3% (w/w);

(b) at least one organic denaturant, wherein the organic denaturant is selected from the group consisting of: 2-pyrrolidinone, N',N'-dimethylacetamide and N',N'-dimethylformamide;

(c) a buffer; and (d) 3 M to 8 M urea, wherein said formulation provides separation of nucleic acids sufficient for use in nucleic acid sequencing.

22. The matrix formulation according to claim 21, wherein the organic denaturant concentration ranges between 5–40% (w/w).

23. The matrix formulation according to claim 21, wherein the organic denaturant concentration ranges between 5%–20% (w/w).

24. A replaceable matrix formulation of claim 21, wherein the urea concentration is 6 M urea.

25. A method of nucleic acid separation using a capillary electrophoresis device comprising the replaceable matrix formulation according to claim 21 and a buffer.

26. The method according to claim 25, wherein the electrophoresis device is operated at a run voltage of between 10 kV–12 kV.

27. The method according to claim 25, wherein the electrophoresis device is operated at a run voltage of at least 12 kV.

28. The method according to claim 25, wherein the electrophoresis device is operated at temperature ranging between 40° C. and 60° C.

29. The method according to claim 28, wherein the electrophoresis device is operated at 44° C.

30. The method according to claim 25, wherein the nucleic acid separation is used in the determination of the molecular size of a nucleic acid.

31. The method according to claim 25, wherein the nucleic acid sample results from the use of dideoxynucleotides.

32. The method according to claim 25, wherein the nucleic acid separation is used in the differential display of messenger RNA (mRNA).

* * * * *